United States Patent [19]
Gansel et al.

[11] Patent Number: 5,794,986
[45] Date of Patent: Aug. 18, 1998

[54] SEMI-DISPOSABLE VENTILATOR BREATHING CIRCUIT TUBING WITH RELEASABLE COUPLING

[75] Inventors: Guy Gansel, San Clemente; Susumu Takabayashi, Oceanside, both of Calif.

[73] Assignee: Infrasonics, Inc., San Diego, Calif.

[21] Appl. No.: 692,378

[22] Filed: Aug. 5, 1996

Related U.S. Application Data

[63] Continuation of Ser. No. 306,373, Sep. 15, 1994, abandoned.

[51] Int. Cl.[6] ................................................. F16L 55/00
[52] U.S. Cl. .......................... 285/173; 385/175; 385/226; 385/247; 385/328; 385/903; 385/921
[58] Field of Search .............................. 285/175, 423, 285/226, 332, 247, 246, 235, 381, 256, 334.5, 903, 173, 328, 921

[56] References Cited

U.S. PATENT DOCUMENTS

| | | | |
|---|---|---|---|
| 3,177,016 | 4/1965 | Holmgren | 285/247 |
| 3,501,171 | 3/1970 | Baron | 285/334.5 X |
| 3,926,458 | 12/1975 | Dryden | 285/235 X |
| 4,035,534 | 7/1977 | Nyberg | 285/381 X |
| 4,133,312 | 1/1979 | Burd | 285/332 X |
| 4,296,949 | 10/1981 | Muetterties et al. | 285/332 X |
| 4,735,441 | 4/1988 | Stephens | 285/332 X |
| 4,803,053 | 2/1989 | Williamson | 285/423 X |
| 5,190,322 | 3/1993 | Hughes | 285/332 X |
| 5,249,610 | 10/1993 | Cassou et al. | 285/256 X |

FOREIGN PATENT DOCUMENTS

| | | | |
|---|---|---|---|
| 400859 | 4/1945 | Italy | 285/334.5 |
| 520698 | 4/1957 | Italy . | |
| 876030 | 8/1961 | United Kingdom | 285/175 |

*Primary Examiner*—Dave W. Arola
*Attorney, Agent, or Firm*—Brown, Martin, Haller & McClain

[57] ABSTRACT

A coupler having a releasable compression fitting connects a length of tubing to a ventilator fitting. The compression fitting allows the tubing to be made of economical and re-usable materials that would otherwise be difficult to attach to a ventilator fitting. The coupler may have a conical end that can be directly attached to a ventilator fitting, or it may have a barbed end over which an elastomeric endpiece is attached, which in turn can be attached to a ventilator fitting. The tubing and coupler may be sterilized and re-used.

6 Claims, 1 Drawing Sheet

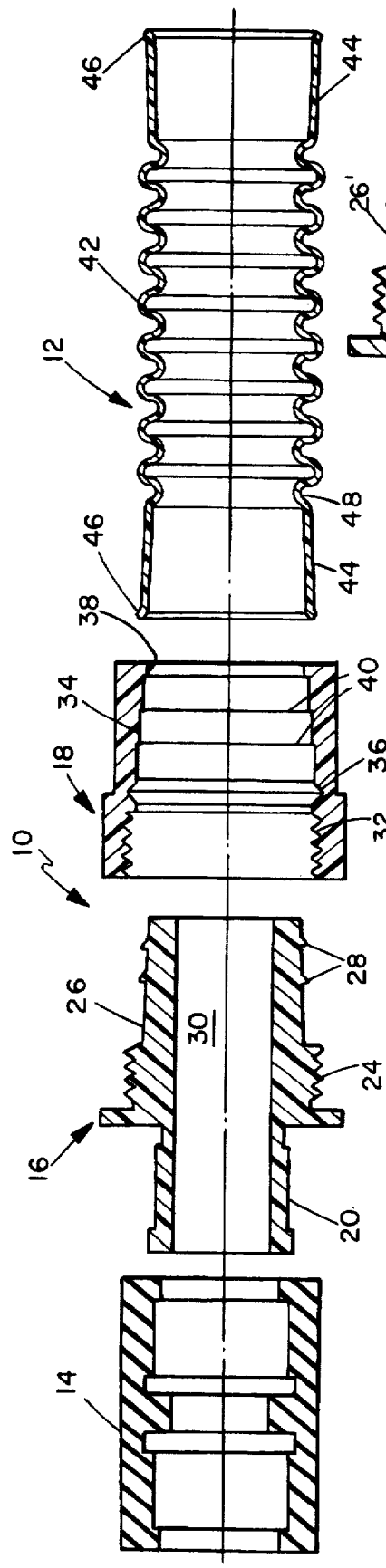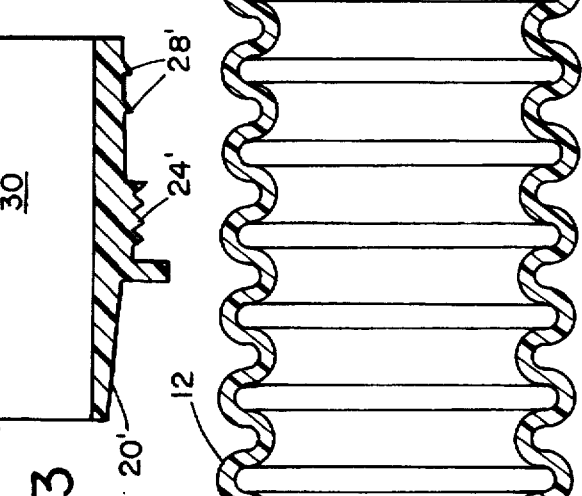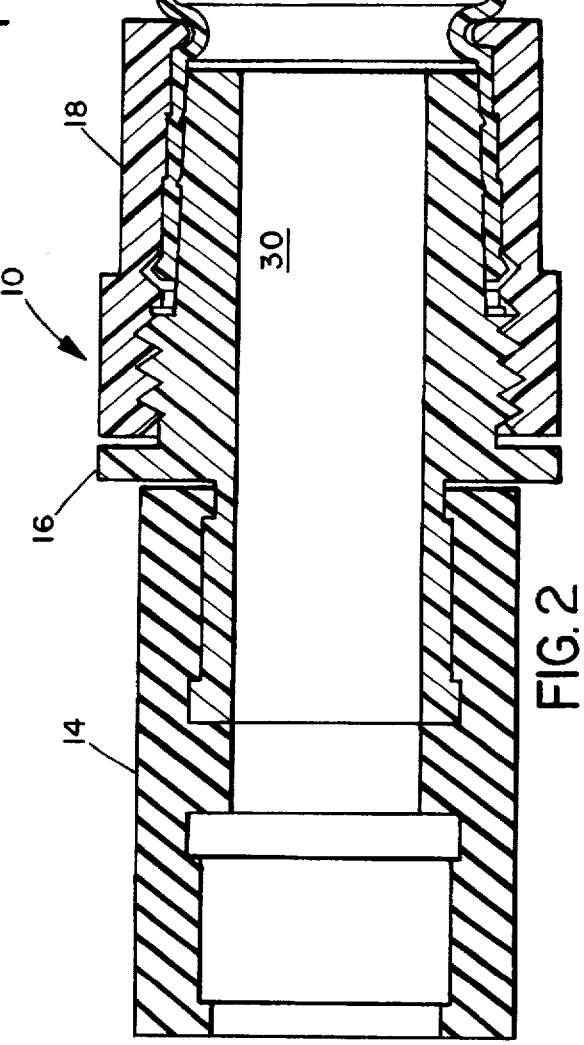
FIG. 1
FIG. 3
FIG. 2

SEMI-DISPOSABLE VENTILATOR BREATHING CIRCUIT TUBING WITH RELEASABLE COUPLING

This is a continuation of application Ser. No. 08/306,373, filed Sep. 15, 1994 now abandoned.

BACKGROUND OF THE INVENTION

The present invention relates generally to medical ventilators and, more specifically, to tubing for use in that portion of the ventilator commonly known as the breathing circuit, which includes the gas supply and control paths and the patient's respiratory system.

The breathing circuit includes an inhalation conduit for delivering gas to the patient, an exhalation conduit for receiving gas from the patient, a patient wye at which the inhalation and exhalation conduits join, and an endotracheal tube or tracheostomy outlet for interfacing the ventilator and patient sides of the breathing circuit. Another conduit may connect the patient wye to the endotracheal tube or tracheostomy outlet. The breathing circuit may also include filters located at the junctions between the exhalation and inhalation conduits and the ventilator housing, a humidifier, and other devices.

Tubular fittings on the patient wye, filters and other portions of the breathing circuit receive the conduits. The conduits include a length of flexible tubing and may also include endpieces for connecting the tubing to the fittings. One commonly used type of fitting is a barbed, cylindrical or frusto-conical projection. The end of the flexible tubing is stretched over this fitting. Alternatively, the end of the flexible tubing may be attached to an elastomeric endpiece, which is, in turn, stretched over the fitting. Another commonly used type of fitting, which is defined by the ISO 5356-1 standard, consists of a rigid frusto-conical female half, into which a male half attached to the end of the flexible tubing is inserted. The male and female halves are formed of a rigid material such as metal. Nevertheless, the friction between the mating halves maintains the connection.

The conduits are an extremely critical aspect of the breathing circuit. The coupling between a conduit and the fitting to which it is connected must withstand tensile stresses to prevent disconnection. The tubing must withstand flexure resulting from normal movement of the patient or ventilator without kinking or collapsing and thus restricting gas flow. Failure of the tubing or coupling can cause damage or death to a patient. In fact, an industry standard attachment test requires that a conduit remain connected to a fitting when a 20 pound tensile force is exerted for 60 seconds. The tubing is typically ribbed, such as by providing corrugation or a continuous spiral rib, to provide sufficient lateral rigidity to prevent the tubing from kinking or collapsing while allowing it to flex laterally and longitudinally. The spiral rib may also be used to attach an endpiece to the tubing in a screw-like manner.

The tubing must either be disposable or sterilizable because medical practitioners typically replace it after about 72 to 168 hours of continuous use. Re-use of tubing through sterilization is increasing in response to concerns over damage to the environment by excessive medical waste. Moreover, re-use of tubing maximizes economy. Sterilization is performed by exposing the tubing to heat ("heat-sterilization") or chemicals ("cold-sterilization"). In heat-sterilization the tubing is typically exposed to steam at 270 degrees Fahrenheit for 20 minutes. Heat-sterilization is preferred because it is easier and more economical to perform than cold-sterilization.

Materials commonly used to form the flexible tubing include silicone rubber, high-density polyethylene, HYTREL®, which is a thermoplastic copolymer produced by DuPont, Inc., and KRATON®, which is a rubbery styrenic block copolymer or thermoplastic elastomer produced by Shell Chemical Company. Silicone rubber is durable and highly elastomeric. It may be reused many times over a lifetime of up to approximately fifteen years by removing it from the fittings, sterilizing it, and reattaching it to the fittings. (Hospitals, however, typically replace such tubing after three to five years because it becomes discolored and gives the appearance of uncleanliness.) In addition, the superior elastomeric and frictional properties of silicone rubber facilitate formation of a strong coupling. However, such tubing is relatively uneconomical because it is formed using a molding process. At present, a conduit between the ventilator and the patient wye made of silicone rubber tubing costs a hospital in the U.S. on the order of $150.

Polyethylene is considerably more economical than silicone rubber because it can be continuously extruded and then cut into the required lengths. Unlike silicone rubber, no expensive molding process is necessary. Nevertheless, it cannot be re-used in conjunction with either heat-sterilization or cold-sterilization. Not only will it melt or deform when subjected to the high temperatures of heat-sterilization, but polyethylene tubing that has been removed from a fitting for any reason cannot be reattached to a fitting because polyethylene has little or no memory. Once stretched over a fitting, such tubing remains permanently stretched and cannot form a coupling with sufficient strength to pass the above-described attachment test. Therefore, polyethylene tubing must be discarded after a single use.

HYTREL® is more economical than silicone rubber, but it is not nearly as economical as polyethylene, both because the material itself is less economical than polyethylene and because it cannot be extruded like polyethylene. Although it can withstand high temperatures without melting or otherwise deforming, the tubing will harden over time when repeatedly heat-sterilized. Moreover, like polyethylene, it is not sufficiently elastomeric to be re-used by connecting it directly to a friction fitting. Silicone rubber endpieces are therefore screwed onto the ends of a length of HYTREL® tubing having a spiral rib and sealed with liquid silicone. The silicone rubber endpieces are sufficiently elastomeric and durable to be repeatedly reconnected to a fitting without degradation in the strength of the resulting coupling. (Silicone rubber has a tensile modulus of approximately 160 psi.)

KRATON® is nearly as economical as polyethylene because it can be extruded using thermoplastic processing methods. Like silicone rubber and HYTREL®, it can withstand the temperatures of heat-sterilization. However, like polyethylene and HYTREL®, it is not sufficiently elastomeric to be re-used by connecting it directly to a friction fitting. (KRATON-D® has a tensile modulus between 400 and 1,000 psi.) Moreover, silicone rubber endpieces cannot be attached to the ends of a length of KRATON® tubing because KRATON® is too soft and pliable to form a strong spiral rib onto which an endpiece could be screwed and too resistant to adhesive bonding for liquid silicone or other adhesives and sealants to be used. (It is believed that a leaching agent in KRATON® prevents adhesion.) In attempts to secure KRATON® tubing directly to a fitting, plastic cable ties and rubber O-rings have been used as crude hose clamps. However, such clamping methods are inconvenient and unreliable. Moreover, successive couplings using the same length of KRATON® tubing become weaker as repeated uses increasingly stretch the tubing. For these reasons, medical practitioners are reluctant to rely on such methods.

It would be desirable to provide a breathing circuit conduit that is not only relatively economical but can also be removed from a fitting, sterilized, and replaced in a fitting multiple times without suffering unacceptable degradation in the strength of the resulting coupling. These problems and deficiencies are clearly felt in the art and are solved by the present invention in the manner described below.

SUMMARY OF THE INVENTION

In one aspect, the present invention comprises a novel coupler for attaching tubing to a conventional ventilator fitting. The coupler is preferably made of a durable, rigid material, such as polycarbonate or polysulfone plastic. One end of the coupler has a releasable compression fitting for gripping the tubing. Unlike a conventional ventilator fitting, in which the tubing is secured by the friction resulting from the forces exerted by the stretched end of elastomeric tubing, the compression fitting of the present invention has two portions between which the end of the tubing is gripped or compressed. The tubing thus remains securely attached regardless of its elastic properties. The end of the tubing may have one or more features that facilitate gripping in the compression fitting. The other end of the coupler has a fitting that can be either directly or indirectly attached to the ventilator fitting. A directly attachable coupler fitting may have, for example, a rigid, conical ISO 5356-1 projection. An indirectly attached coupler fitting may have a barbed projection over which one end of an elastomeric endpiece can be stretched, with the other end stretched over the ventilator fitting.

The tubing and coupling may be re-used using either heat or cold-sterilization. Similarly, the coupler may be sterilized and re-used. Medical waste and its resulting environmental damage are thus minimized.

Although the tubing may be made of any suitable material, the coupler is particularly useful if the tubing is made of a material that cannot otherwise be readily attached to a ventilator fitting. The tubing may have elastic properties too poor to allow formation of a secure connection by stretching it over a ventilator fitting. The tubing may have other physical properties that prevent its attachment to an elastomeric endpiece using non-mechanical means, such as adhesive bonding, heat fusing, sonic welding, and the like, or using an integrally formed coupling member such as a spiral rib. For example, a tube made of KRATON® is heat-sterilizable, but it cannot be stretched over a ventilator fitting to form a secure connection, cannot be adhesively bonded to a silicone rubber endpiece, and cannot be provided with a strong spiral rib.

The conduit defined by the combination of the releasable coupler and the tubing may be characterized as "semi-disposable" because the durable coupler may be re-used over a lifespan of many years while the tubing may be re-used for a somewhat shorter period and then discarded. For example, a tube made of KRATON® may be re-used until it becomes discolored. The combination of tubing that is both economical and semi-reusable with a highly reusable coupler both increases cost savings to health care providers and reduces the amount of medical waste that is discarded. The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated the accompanying drawings, wherein:

FIG. 1 is a sectional view of the present invention; and

FIG. 2 is an enlarged sectional view similar to FIG. 1, showing the coupling between the two lengths of tubing; and FIG. 3 is a sectional view of an alternative inner coupling member having a conical male fitting half.

DESCRIPTION OF PREFERRED EMBODIMENTS

As illustrated in FIG. 1, a coupler 10 joins a length of tubing 12 to an endpiece 14. Coupler 10 comprises an inner coupling member 16 and an outer coupling member 18, both of which are preferably made of a durable, heat-sterilizable plastic, such as polycarbonate. Tubing 12 may be any suitable length.

Inner coupling member 16 has a stretch fitting 20 over which the proximal end of endpiece 14, which is preferably made of silicone rubber, is stretched. Inner coupling member 16 also has an inner coupling member threaded portion 24 and a tapered or frusto-conical inner coupling member grip surface 26. Inner coupling member grip surface 26 has a plurality of male circumferential barbs 28. A bore 30 extends through inner coupling member 16.

Outer coupling member 18 has an outer coupling member threaded portion 32 for mating with inner coupling member threaded portion 24. Outer coupling member 18 also has an outer coupling member grip surface 34. Outer coupling member grip surface 34 has a circumferential groove 36, a circumferential coupling lip 38, and a plurality of female circumferential barbs 40.

Tubing 12 has a corrugated portion 42 and a tapered or frusto-conical non-corrugated portion 44. Non-corrugated portion 44 has a circumferential tubing lip 46. Suitable material for tubing 12 has a tensile modulus of between approximately 400 and 1,000 and can withstand the temperatures of heat-sterilization (270 degrees for 20 minutes) without deforming. It should also be economical in relation to silicone rubber, which would be the ideal material for ventilator breathing circuit tubing were cost not a factor. Tubing 12 is preferably made of KRATON® thermoplastic rubber copolymer. Not only is such material relatively economical but the tubing can be formed using relatively economical thermoplastic processes. As will be recognized by persons of skill in the art, the corrugations and other surface features of tubing 12 may be formed using a blow-molding process in conjunction with an extrusion process.

In other embodiments, tubing 12 may be made of a material that has characteristics that, like those of KRATON®, prevent its direct connection to a ventilator fitting. The material may, for example, have poor elasticity, i.e., a tensile modulus over 400. The material may not, for example, be adhesively bondable to an elastomeric endpiece due to a low porosity, e.g., less than one percent, or due to the presence of a leaching agent.

To connect tubing 12 to coupler 10, non-corrugated portion 44 is inserted through circumferential coupling lip 38 into outer coupling member grip portion 34 until circumferential tubing lip 46 is received in circumferential coupling groove 36. The mating of circumferential tubing lip 46 and circumferential coupling groove 36 provides a first point of engagement that aligns the resulting coupling between coupler 10 and tubing 12. Circumferential coupling lip 38 is received in the first groove 48 of corrugated portion 42. The mating of circumferential coupling lip 38 and first groove 48 provides a primary point of engagement that aligns coupling 18 to tubing 12. Inner coupling member grip portion 26 is then inserted through outer coupling member threaded portion 32 into non-corrugated portion 44 of tubing 12 until inner coupling member threaded portion 24 contacts outer coupling member threaded portion 32. Inner and outer coupling members 16 and 18 are rotated with respect to one another to engage threaded portions 24 and 32. In response to this rotation, inner coupling member grip surface 26 moves closer to outer coupling member grip surface 34 because grip surfaces 26 and 34 are tapered. As grip surfaces 26 and 34 approach one another they compress non-corrugated portion 44 of tubing 12 between them. This compression provides the most important point of engagement that strengthens the coupling between coupler 10 and tubing 12. In addition, male circumferential barbs 28 are aligned with female circumferential barbs 40 when threaded portions 24 and 32 are fully engaged. This alignment maximizes the strength of the main point of engagement. Unlike a connection between an ordinary stretch fitting and a tube, the strength of the resulting coupling of the present invention is not dependent upon the elasticity of tubing 12. The connection will remain strong despite the relatively inelastic properties of KRATON® tubing.

Once assembled, the conduit comprising tubing 12, endpiece 14 and coupler 10 may be substituted for any of conventional conduit used in the breathing circuit of a ventilator (not shown). The free end of endpiece 14 may be connected to any conventional stretch fitting in the breathing circuit in the manner known in the art. The free end of tubing 12 may be connected to another coupler (not shown) that is identical to coupler 10 and its endpiece may be connected to another stretch fitting in the breathing circuit.

The present invention may be removed from the ventilator breathing circuit and sterilized as often as the medical practitioner requires. Coupler 10 and endpiece 14 will not degrade for a period of many years of typical hospital use. Although tubing 12 may last nearly as long without degradation, it has been found that tubing 12, because it is made of KRATON®, may discolor and assume the appearance of uncleaniness after a period of between six months and one year of typical hospital use. Tubing 12 may then be discarded and replaced.

In an alternate embodiment, illustrated in FIG. 3, an inner coupling member 16' has a conical fitting 20' in accordance with ISO standard 5356-1. Inner coupling member 16' may be used in coupler 10 in the same manner as inner coupling member 16. Inner coupling member 16' has a bore 30', an inner coupling member threaded portion 24', and an inner coupling member grip surface 26' with a plurality of male circumferential barbs 28'. Conical fitting 20' may be directly connected to a mating ventilator fitting; no intermediate elastomeric endpiece is necessary.

The present invention strikes a novel balance between waste reduction and economy. The amount of waste produced using the present invention in a given period of time is substantially less than would be produced using disposable polyethylene tubing because the KRATON® tubing can be reused multiple times. The cost of ventilator breathing circuit conduits made in accordance with the present invention is substantially less than that of conduits made of silicone rubber because the KRATON® tubing is relatively economical and the coupler can be reused indefinitely.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

I claim:

1. A conduit for a ventilator breathing circuit, comprising:
   tubing made of a thermoplastic material having a tensile modulus greater than 400 psi and that does not deform when subjected to a temperature of 270° F. for 20 minutes;
   a compression coupler including at least two concentrically disposed tubular members selectably movable in an axial direction relative to one another, said tubular members having respective surfaces radially adjacent to one another and movable in a radial direction with respect to one another in response to relative axial movement of said tubular members for compressively engaging a portion of said tubing between said respective surfaces, one of said tubular members having a fitting; and
   an elastomeric endpiece stretchably connected over said fitting and frictionally gripping said fitting, said elastomeric endpiece having a tensile modulus less than 200 psi.

2. The conduit claimed in claim 1, wherein:
   said tubing is made of KRATON; and
   said elastomeric endpiece is made of silicone rubber.

3. The conduit claimed in claim 1, wherein at least one of said tubular members has a frusto-conical surface in contact with said portion of said tubing.

4. The conduit claimed in claim 3, wherein said compression coupler comprises:
   a tubular inner coupling member having a frusto-conical inner coupling member outer surface, an inner coupling member first end, an inner coupling member second end, and an inner coupling member threaded portion in said inner coupling member outer surface, said inner coupling member second end having a fitting;
   a tubular outer coupling member having a frusto-conical outer coupling member inner surface, an outer coupling member first end, an outer coupling member second end, and an outer coupling member threaded portion on said outer coupling member inner surface for mating with said inner coupling member threaded portion; and
   said portion of said tubing is compressively engaged between said outer coupling member inner surface and said inner coupling member outer surface when said outer coupling member threaded portion is threadably mated with said inner coupling member threaded portion.

5. The conduit claimed in claim 4, wherein said portion of said tubing has a lip at the tube end for engaging a circumferential slot on said outer coupling member inner surface.

6. The conduit claimed in claim 4, wherein:
   said inner coupling member outer surface has male circumferential barbs; and
   said outer coupling member inner surface has female circumferential barbs substantially aligned with said male circumferential barbs when said outer coupling member threaded portion is threadably mated with said inner coupling member threaded portion.

* * * * *